United States Patent
Gendler et al.

(10) Patent No.: US 6,576,249 B1
(45) Date of Patent: Jun. 10, 2003

(54) BONE PUTTY AND METHOD

(76) Inventors: El Gendler, 415 Georgina Ave., Santa Monica, CA (US) 90402; Eli Gendler, 415 Georgina Ave., Santa Monica, CA (US) 90402; Simon Gendler, 6346 Warner Dr., Los Angeles, CA (US) 90048

( * ) Notice: Subject to any disclaimer, the term of this patent is extended or adjusted under 35 U.S.C. 154(b) by 0 days.

(21) Appl. No.: 09/711,716

(22) Filed: Nov. 13, 2000

(51) Int. Cl.$^7$ .......................... A61L 15/64; A61K 35/32
(52) U.S. Cl. ................... 424/423; 424/422; 424/426; 424/549; 514/801; 514/802; 623/16; 623/13
(58) Field of Search ................ 424/422, 423, 424/426, 549; 514/801, 802; 623/16, 13

(56) References Cited

U.S. PATENT DOCUMENTS

| | | | |
|---|---|---|---|
| 4,172,128 A | * 10/1979 | Thiele et al. ................. | 424/95 |
| 4,932,973 A | 6/1990 | Gendler ................... | 623/23.63 |
| 5,073,373 A | 12/1991 | O'Leary et al. ............ | 424/422 |
| 5,092,887 A | 3/1992 | Gendler ...................... | 128/898 |
| 5,284,655 A | 2/1994 | Bogdansky et al. ......... | 426/602 |
| 5,290,558 A | 3/1994 | O'Leary et al. ............. | 424/422 |
| 5,306,304 A | 4/1994 | Gendler ................... | 623/23.63 |
| 5,314,476 A | 5/1994 | Prewett et al. ........... | 623/23.63 |
| 5,464,439 A | 11/1995 | Gendler ...................... | 128/898 |
| 5,507,813 A | 4/1996 | Dowd et al. ............. | 623/23.63 |
| 5,510,396 A | 4/1996 | Prewett et al. .............. | 523/113 |
| 5,556,430 A | 9/1996 | Gendler ...................... | 128/898 |
| 5,904,716 A | 5/1999 | Gendler ...................... | 424/423 |
| 6,030,635 A | 2/2000 | Gertzman et al. .......... | 424/423 |

* cited by examiner

Primary Examiner—Christopher S. F. Low
Assistant Examiner—Chih-Min Kam
(74) Attorney, Agent, or Firm—Leydig, Voit & Mayer, Ltd

(57) ABSTRACT

A method for the preparation of bone gel and bone putty which comprises producing a viscous supernatant by dissolving demineralized bone matrix in water or a solution comprising water and at least one component normally found in human blood serum, at a temperature above about 25° C. Agitation and/or ultrasound or pressure accelerates dissolution of the demineralized bone. The resulting viscous supernatant is cooled, then mixed with demineralized or non-demineralized bone matrix particles to form a gel-like suspension or putty-like material.

29 Claims, No Drawings

BONE PUTTY AND METHOD

FIELD OF THE INVENTION

This invention pertains to a bone matrix suspension in forms suitable for surgical grafting or other medical uses and a method for making same.

BACKGROUND OF THE INVENTION

Malleable bone putty or bone gel is used to correct surgical defects that may be caused by trauma, pathological disease, surgical intervention or other situations where defects need to be managed in osseous surgery. It is important to have the defect filler in the form of a stable, viscous gel or putty to facilitate the placement of the bone growth medium into the surgical site which is usually uneven in shape and depth. The surgeon will take the gel or putty on a spatula or other instrument and trowel it into the site or take it in his/her fingers to shape the bone inducing material into the proper configuration to fit the site being corrected.

It is well known in the art that for several decades surgeons have used a patient's own blood as a vehicle in which to mix the patient's bone chips or bone powder, or demineralized bone powder so as to form a defect filling paste. Blood is a useful carrier because it is available from the bleeding operative site, is non-immunogenic to the patient and contains bone morphogenic proteins which facilitate wound healing through new bone growth. However, stored blood from other patients has the deficiencies that any blood transfusion would have such as blood type compatibility, possibility of transmission of disease and unknown concentration of bone morphogenic proteins (BMP) which are to a great extent dependent upon the age of the donor.

While blood contains from forty percent (40%) to fifty percent (50%) cell mass, it is a satisfactory carrier for demineralized bone powder because it contains both mono- and polysaccharides which contribute to the blood viscosity and provide the bulk viscosity to the paste created by mixing the bone powder and blood. Specific monosaccharides in blood are glucose at a concentration of 60–100 mg/100 ml (0.1%) and polysaccharides such as hexose and glucosamine at approximately 0.1%. Glucuronic acid is also present at approximately 0.4–1.4 mg/100 ml (average 0.01%).

The problems inherent with using the patient's blood as a carrier for demineralized bone powder are the difficulties of mixing the same at the operating site, the difficulty in obtaining a bone paste consistency which can be easily applied to the surgical area, the guesswork in mixing a usable composition at the site and the problem of having a bone paste or gel which will promote optimum bone replacement growth and not be carried away by the body fluids at the operation site or simply fall out of the bone defect site. In an attempt to solve these and other problems, there have been a number of other attempts using other alternative mixtures and compositions.

Demineralized allograft bone matrix (DBM) is produced from banked human bone taken from cadavers. Demineralized allograft bone is usually available in a lyophilized or freeze dried and sterile form—such as cubes, shavings, or powder—to provide for extended shelf life. The bone in this form is usually very coarse and dry and is difficult to manipulate by the surgeon. One solution to use such freeze dried bone has been provided in the form of a gel, GRAFTON®, a registered trademark of Osteotech Inc., which is a simple mixture of glycerol and lyophilized, demineralized bone powder of a particle size in the range of 0.1 cm to 1.2 cm (1000 microns to 12,000 microns) as is disclosed in U.S. Pat. No. 5,073,373.

GRAFTON® works well to allow the surgeon to place the allograft bone material at the site. However, the carrier, glycerol, has a very low molecular weight (92 Daltons) and is very soluble in water—the primary component of the blood which flows at the surgical site. Glycerol also experiences a marked reduction in viscosity when its temperature rises from room temperature (typically 22° C. in an operating room) to the temperature of the patient's tissue, typically 37° C. This combination of high water solubility and reduced viscosity causes the allograft bone material to be "runny" and to flow away from the site almost immediately after placement; this prevents the proper retention of the bone within the site as carefully placed by the surgeon.

These problems with GRAFTON® gel have been attempted to be resolved by using a much larger particle size of allograft bone, specifically lamellae or slivers of bone created by milling or slicing the bone before mixing it with the glycerol carrier. This improves both the bulk viscosity and the handling characteristics of the mixture but still leaves the problem of the fast rate of dissipation of the carrier and some bone due to the solubility of the glycerol carrier. The larger particles of demineralized bone may also retard the development of new bone by the patient because the large bony lamellae do not pack as well as the smaller grainy particles of bone. This will leave more open space and could lengthen the tine required to grow new bone and properly fill the defect. Another deficiency of using the bony lamellae is that the ends of the bony fragments are uneven and when packed into the surgical defect, leave uneven filaments of bone protruding out from the defect which can compromise the healing rate.

U.S. Pat. No. 5,290,558 discloses a flowable demineralized bone powder composition using a osteogenic bone powder with a large particle size ranging from about 0.1 to about 1.2 cm, mixed with a low molecular weight polyhydroxy compound possessing from 2 to about 18 carbons including a number of classes of different compounds such as monosaccharides, disaccharides, water dispersible oligosaccharides and polysaccharides.

Hence, the advantages of using the smaller bone particle sizes as disclosed in the U.S. Pat. No. 5,073,373 gel patent were compromised by using bone lamellae in the shape of threads or filaments and retaining the low molecular weight glycerol carrier. This later prior art is disclosed in U.S. Pat. Nos. 5,314,476 and 5,507,813, and the tissue forms described in these patents are known commercially as the GRAFTON® Putty and Flex, respectively.

The use of the very low molecular weight glycerol carrier also requires a very high concentration of glycerol to be used to achieve the bulk viscosity. Glycerol and other similar low molecular weight organic solvents are toxic and irritating to the surrounding tissues. Furthermore glycerol has been reported to be specifically neurotoxic and this problem is compounded when the concentration of glycerol is at the 20–95% level, as disclosed in U.S. Pat. No. 5,073,373.

Another attempt to solve the bone composition problem is shown in U.S. Pat. No. 4,172,128, which discloses demineralized bone material mixed with a carrier used to reconstruct tooth or bone material, and made by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35° C. and will solidify when brought down to body temperature. Example 25 of the patent notes that mucopolysaccharides produce pronounced ionotropic effects and that hyaluronic acid is particularly responsible for spatial cross-linking. Unfortunately this bone gel is difficult to manufacture and requires a pre-molded gel form.

U.S. Pat. No. 4,191,747 teaches a bone defect treatment with coarsely ground, denatured bone meal freed from fat and ground into powder. The bone meal is mixed with a polysaccharide in a solution of saline and applied to the bone defect site.

Another prior art product is the formulation of demineralized allograft bone particles in collagen. Both bovine and human collagen have been used for this application. Bovine collagen carries the risk of an immunogenic reaction by the recipient patient. Recently, it has been found that a disease of cattle, bovine spongioform encephalopathy (BSE), is transmitted from bovine tissue to humans. Thus, bovine tissue carries a risk of disease transmission and is not a desirable carrier for allograft tissue.

Human collagen is free of these animal based diseases. However, collagen absorbs slowly in the human body, particularly in a bony site with usually a low degree of vascularity. The slow absorption of collagen can delay the growth of new bone and result in the formation of scar tissue at the site. This could result in a non-bony healing and a result with much less tensile strength.

U.S. Pat. No. 6,030,635 describes a method for making a bone putty or gel in which bone powder is suspended in a carrier that is selected from the group consisting of sodium hyaluronate, chitosan and N,O-carboxymethylchitosan, in water solution. The use of other hydrogels is also disclosed. A disadvantage of such a composition is that it employs as a carrier synthetic components that may not be well tolerated in vivo.

Accordingly, the prior art as embodied in the glycerol and other carrier based technology to deliver demineralized allograft bone to a surgical osseous site is replete with problems and only partially addresses the problems inherent in the correcting surgical defects.

A need exists for a bone gel or putty free from the disadvantages of the prior art.

BRIEF SUMMARY OF THE INVENTION

A bone gel or putty has been discovered that uses aqueous dissolved demineralized bone as the carrier in which bone particles are suspended. The carrier may also comprise additional components such as those normally found in blood serum. The carrier is non-toxic and does not adversely impact the patient. These and other advantages of the present invention, as well as additional inventive features, will be apparent from the description of the invention provided herein.

The present invention also provides an easy method for the production of bone gel or bone putty that is biocompatible, non-inflammatory, capable of inducing osteogenesis, and has the ability to be ultimately reabsorbed by the body and replaced with natural bone. Further, the aforementioned gel or putty can be made extremely malleable while retaining its structural and dimensional integrity both prior to and after hydration and additionally possessing significant tensile strength.

DETAILED DESCRIPTION OF THE INVENTION

Method for Making the Carrier

The aqueous dissolved demineralized bone used as the carrier may be formed in any advantageous manner. For example, a supernatant may be formed by dissolving demineralized allograft bone matrix, in the form of cubes, shavings, or powders, in either water or a solution comprising water and at least one component normally found in animal blood serum (e.g., sodium chloride, potassium phosphate, sodium bicarbonate, or the like) at a temperature of above about 25° C. Preferably, dissolution is enhanced by the use of agitation and/or ultrasound. The dissolution may also be enhanced by use of pressure. Preferably the pressure will be at least about 15 psi, for a period of time. The resulting viscous supernatant is then cooled and mixed with demineralized or non-demineralized bone powder or shavings to form a gel-like or putty-like suspension.

Most preferably the supernatant is obtained by heating to a temperature between about 85° C. and about 100° C. As the demineralized bone dissolves in the water, a viscous supernatant is formed from the demineralized bone. The bone dissolution is continued under the elevated temperature for a period of time sufficient to generate a supernatant having a viscosity above about 1 centipoise; more particularly, the heating is continued to the point where a thick, viscous liquid has been formed, which usually takes place between about 24 and about 120 hours. The supernatant is then allowed to cool.

If the heated solution is subjected to an elevated pressure of at least about 15 psi, more preferably between about 15 psi and about 90 psi, the bone is dissolved more readily. The use of pressure to dissolve the demineralized bone matrix is faster, in that the process, depending on the amount of pressure used, usually only needs to be carried out from between about 1 hour to about 8 hours. The further advantage lies in that there may not need to be any mechanical agitation, as the elevated pressure compensates for this.

Once the supernatant is obtained, the supernatant is then cooled. Once cooled, the viscous supernatant is mixed with either demineralized or non-demineralized bone powder or shavings. As this is done, the mixture will achieve, at first, a gel-like texture. At this point, a bone gel has been formed from the mixture of a supernatant with suspended demineralized bone particles and demineralized or non-demineralized bone powder or shavings. However, more demineralized or non-demineralized bone powder or shavings may be added in order to achieve a putty-like texture.

Usually the amount of dissolved demineralized bone will be from about 0.5 to about 25 percent, by weight, based on the total weight of water and bone, preferably from about 5 to about 10 percent.

The demineralized bone used to make the carrier may be in any physical form, such as chips, shavings or particles. The form of the demineralized bone used to make the carrier is not critical, as it ultimately will be dissolved. The use of smaller particles will aid in the dissolution process.

Sufficient demineralized bone is dissolved to increase the viscosity of the water. Preferably the viscosity is increased to from about 2 to about 100 centipoises, preferably from about 40 to about 200 centipoises. Alternatively sufficient demineralized bone is dissolved to convert the carrier into a gel or gel-like structure.

The water may be sterile water for injection or sterile saline solution or may comprise other components, such as those normally found in blood, such as BSS balanced salt solution, containing 140 mM NaCl, 5.4 mM KCl, at a pH of 7.6. Soluble calcium can be attracted to the surgical site by using a sodium phosphate buffer of pH 7.2 in lieu of the isotonic saline. The phosphate buffer will attract calcium cations to the site from the surrounding healthy bone and create an equilibrium concentration of the calcium precisely at the site of healing where it is most desirable to grow new bone.

The Suspension

To form the desired bone putty or gel, bone powder or shavings are added to form a gel-like or putty-like suspension. The bone that is added may be demineralized or non-demineralized bone, or a mixture thereof, and may be in the physical form of chips, shavings or powder. Preferably the bone has an average particle size of from about 10 to about 850 microns, more preferably from about 250–500 microns.

The amount of suspended bone that is present in the final product usually will be from about 5 to about 50 percent by weight, based on the total weight of the suspension, preferably from about 7 to about 30 percent, and most preferably from about 10 to about 20 percent.

The following examples further illustrate the present invention but, of course, should not be construed as in any way limiting its scope.

EXAMPLE 1

This example demonstrates a novel method of making a bone gel with a useful bulk viscosity and optimum bioabsorbability.

Demineralized bone powder with particle size of 45–125 µm is placed in distilled water boiling at 100° C. The solution is constantly agitated by magnetic stirring and/or ultrasound for 72 hours, at which point a viscous supernatant has been produced. The supernatant is then set out for several hours to cool, and then mixed with demineralized bone powder to form a gel-like suspension.

EXAMPLE 2

This example demonstrates a novel method of making a bone putty with a useful bulk viscosity and optimum bioabsorbability.

Demineralized bone powder with particle size of 45–125 µm is placed in distilled water boiling at 100° C. The solution is constantly agitated by magnetic stirring and/or ultrasound for 72 hours, at which point a viscous supernatant has been produced. The supernatant is then set out for several hours to cool, and then mixed with demineralized bone shavings to form a putty-like material.

EXAMPLE 3

This example demonstrates a novel method of making a bone gel with a useful bulk viscosity and optimum bioabsorbability.

Demineralized bone powder with a particle size of 45–125 µm is placed in distilled boiling water and autoclaved at a temperature of 110–115° C. and at a pressure of 20–22 psi for about 3 hours, at which point a viscous supernatant is produced. The supernatant is then set out for several hours to cool, and then mixed with demineralized bone powder to form a gel-like suspension.

EXAMPLE 4

This example demonstrates a novel method of making a bone putty with a useful bulk viscosity and optimum bioabsorbability.

Demineralized bone powder with a particle size of 45–125 µm is placed in distilled boiling water and autoclaved at a temperature of 110–115° C. and at a pressure of 20–22 psi for about 3 hours, at which point a viscous supernatant is produced. The supernatant is then set out for several hours to cool, and then mixed with demineralized bone shavings to form a putty-like material.

All of the references cited herein, including patents, patent applications, and publications, are hereby incorporated in their entireties by reference.

While this invention has been described with an emphasis upon preferred embodiments, variations of the preferred embodiments can be used, and it is intended that the invention can be practiced otherwise than as specifically described herein. Accordingly, this invention includes all modifications encompassed within the spirit and scope of the invention as defined by the following claims.

What is claimed is:

1. A method for preparing a suspension of bone particles comprising
    (a) producing a supernatant by contacting demineralized bone matrix with water at an elevated temperature sufficient to aid in the dissolution of the bone matrix, for a period of time sufficient to provide a supernatant having a viscosity above 2 centipoise;
    (b) cooling the resulting supernatant to about room temperature; and
    (c) mixing the resulting supernatant with an amount of demineralized or non-demineralized bone matrix particles sufficient to form a suspension of the bone matrix particles.

2. The method of claim 1 wherein during step (a) the demineralized bone matrix is contacted:
    (i) with water at a temperature above about 25° C. with agitation; or
    (ii) with water at a temperature above about 25° C. and at a pressure above about 15 psi.

3. The method according to claim 2, wherein during step (i), the water and demineralized bone matrix are maintained at an average temperature of at least 85° C.

4. The method according to claim 3, wherein step (i) is carried out for at least 24 hours.

5. The method according to claim 4, wherein during step (i), the water and demineralized bone matrix are maintained at an average temperature of at least 100° C.

6. The method according to claim 2, wherein step (i) is carried out until the viscosity of the heated supernatant is at least 2 centipoise.

7. The method according to claim 2, wherein during step (ii), the water and demineralized bone matrix are maintained at an average temperature of at least 105° C.

8. The method according to claim 7, wherein during step (ii), the water and demineralized bone matrix are subjected to pressure of at least 30 psi.

9. The method according to claim 8, wherein step (ii) is carried out for at least 1 hour.

10. The method according to claim 2, wherein step (ii) is carried out until the viscosity of the heated supernatant is at least 2 centipoise.

11. A method for preparing a bone gel or bone putty comprising
    (a) producing a supernatant by dissolving demineralized bone matrix in:
        (i) a solution comprising water and human blood serum or any component thereof at a temperature of above about 25° C. with agitation; or (ii) a solution comprised of water and human blood serum or any component thereof at a temperature of at least about 25° C. and a pressure of at least about 15 psi;

for a period of time sufficient to provide a supernatant having a viscosity above about 2 centipoise;

(b) cooling the resulting supernatant to about room temperature; and (c) mixing the resulting supernatant with an amount of demineralized or non-demineralized bone matrix particles sufficient to form a bone gel or bone putty.

12. The method according to claim 11, wherein the solution of (a) comprises water and a human blood serum component selected from the group consisting of sodium chloride, potassium phosphate, and sodium bicarbonate.

13. The method according to claim 11, wherein during step (a)(i), the solution and demineralized bone matrix are maintained at an average temperature of at least 85° C.

14. The method according to claim 13, wherein step (a)(i) is carried out for at least 24 hours.

15. The method according to claim 14, wherein during step (a)(i), the water and demineralized bone matrix are maintained at an average temperature of at least 100° C.

16. The method according to claim 11, wherein step (a)(i) is carried out until the viscosity of the heated supernatant is at least 2 centipoise.

17. The method according to claim 11, wherein during step (a)(ii), the water and demineralized bone matrix are maintained at an average temperature of at least 105° C.

18. The method according to claim 17, wherein during step (a)(ii), the water and bone composition is subjected to pressure of at least 30 psi.

19. The method according to claim 18, wherein step (a)(ii) is carried out for at least 1 hour.

20. The method according to claim 11, wherein step (a)(ii) is carried out until the viscosity of the heated supernatant is at least 2 centipoise.

21. The method according to claim 1, wherein the particle size of the bone matrix used is between about 10 and about 850 microns.

22. The method according to claim 1, wherein the particle size of the bone matrix used is between about 45 and about 125 microns.

23. The method according to claim 1, wherein the amount of suspended bone that is present in the final product is from about 5% to about 50% by weight.

24. The method according to claim 22, wherein the particle size of the bone matrix used is between about 10 and about 850 microns.

25. The method according to claim 22, wherein the particle size of the bone matrix used is between about 10 and about 850 microns.

26. The method according to claim 22, wherein the amount of suspended bone that is present in the final product is from about 5% to about 50% by weight.

27. The method according to claim 11, wherein the particle size of the bone matrix used is between about 10 and about 850 microns.

28. The method according to claim 11, wherein the particle size of the bone matrix used is between about 45 and about 125 microns.

29. The method according to claim 11, wherein the amount of suspended bone that is present in the final product is from about 5% to about 50% by weight.

* * * * *

UNITED STATES PATENT AND TRADEMARK OFFICE
CERTIFICATE OF CORRECTION

PATENT NO. : 6,576,249 B1
DATED : June 10, 2003
INVENTOR(S) : Gendler et al.

It is certified that error appears in the above-identified patent and that said Letters Patent is hereby corrected as shown below:

Column 1,
Line 67, "or greater" should be inserted after "25°C., 25°C., 15 psi, and 2 centipose".

Column 6,
Lines 35, 37 and 38, respectively, "above" should be deleted.
Lines 35, 37 and 38, respectively, "or greater" should be inserted after "25° C., 25° C., and 15 psi,".

Column 7,
Lines 3, 4 and 6, respectively, "or greater" should be inserted after "25°C., 25°C., 15 psi, and 2 centipoise".
Line 3, both instances of "at least" should be deleted.
Line 6, "above" should be deleted.

Column 8,
Lines 12 and 31, "matrix particles" should be inserted after "bone".
Lines 14-16, claim 24, the dependency should be upon claim 2.
Lines 17-19, claim 25, the dependency should be upon claim 2.
Lines 18-19, "about 10 and about 850 microns" should be deleted and "about 45 and about 125 microns" should be inserted therefor.

Signed and Sealed this

Twentieth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,576,249 B1
DATED : June 10, 2003
INVENTOR(S) : Gendler et al.

It is certified that error appears in the above-identified patent and that said Letters Patent is hereby corrected as shown below:

Column 6,
Lines 35, 37 and 38, respectively, "above" should be deleted.
Lines 35, 37 and 38, respectively, "or greater" should be inserted after "25° C., and 15 psi,"
Line 67, "or greater" should be inserted after "25°C., 15 psi, and 2 centipose".

Column 7,
Lines 3, 4 and 6, respectively, "or greater" should be inserted after "25°C., 15 psi, and 2 centipoise".
Line 3, both instances of "at least" should be deleted.
Line 6, "above" should be deleted.

Column 8,
Lines 12 and 31, "matrix particles" should be inserted after "bone".
Lines 14-16, claim 24, the dependency should be upon claim 2.
Lines 17-19, claim 25, the dependency should be upon claim 2.
Lines 18-19, "about 10 and about 850 microns" should be deleted and "about 45 and about 125 microns" should be inserted therefor.

This certificate supersedes Certificate of Correction issued July 20, 2004.

Signed and Sealed this

Twenty-first Day of September, 2004

JON W. DUDAS
*Director of the United States Patent and Trademark Office*